United States Patent [19]
Behrens et al.

[11] Patent Number: 5,696,119
[45] Date of Patent: Dec. 9, 1997

[54] (2-QUINOXALINYLOXY) PHENOXYPROPANOIC ACIDS AND RELATED DERIVATIVES AS ANTICANCER AGENTS

[75] Inventors: Carl Henry Behrens, Newark, Del.; Betsy Ann Dusak, Secane, Pa.; Barbara Ann Harrison; Michael James Orwat, both of Wilmington, Del.

[73] Assignee: The DuPont Merck Pharmaceutical Company, Wilmington, Del.

[21] Appl. No.: 367,481

[22] Filed: Dec. 28, 1994

Related U.S. Application Data

[63] Continuation of Ser. No. 991,525, Dec. 15, 1992, abandoned.

[51] Int. Cl.$^6$ .................................................. A61K 31/495
[52] U.S. Cl. ........................................ 514/249; 544/354
[58] Field of Search ............................... 544/354; 514/249

[56]  References Cited

U.S. PATENT DOCUMENTS

| 4,609,396 | 9/1986 | Fawzi | 71/92 |
|---|---|---|---|
| 4,629,493 | 12/1986 | Ura et al. | 71/92 |
| 4,655,819 | 4/1987 | Serban et al. | 71/92 |
| 4,803,273 | 2/1989 | Serban et al. | 544/354 |
| 4,944,790 | 7/1990 | Moser et al. | 71/92 |
| 5,035,736 | 7/1991 | Hagen et al. | 71/98 |
| 5,078,780 | 1/1992 | Moser et al. | 71/98 |

FOREIGN PATENT DOCUMENTS

| 2007173 | 7/1990 | Canada . |
|---|---|---|
| 2007709 | 7/1990 | Canada . |
| 0023785 | 2/1981 | European Pat. Off. . |
| 0323727 | 7/1989 | European Pat. Off. . |
| 0456067A1 | 11/1991 | European Pat. Off. . |
| 62-108802 | 5/1987 | Japan . |
| 2202223 | 9/1988 | United Kingdom . |
| WO9104969 | 4/1991 | WIPO . |

OTHER PUBLICATIONS

Makino et al. (1986) J. Pesticide Sci., 11: 469–472.

Georgi–Renault et al. (1989) J. Pharm. Sci., 78: 267–273.

Martin et al, *Cancer Research*, 46, p. 2189 (1986).

Branda et al. (1988) Biochemical Pharmacology, 37: 4557–4564.

Branda et al. (1989) Biochemical Pharmacology, 38: 3521–3526.

Patel et al. (1991) Eur. J. Biochem., 197: 597–604.

Tsuda et al. (1990) Carcinogenesis, 11:549–552.

Gauze et al. (1957) Actinomadura Reciticatena SP. Nov: 7–14 81st AACR, (1990) ABS 1052, Pharmaprojects.

*Primary Examiner*—Emily Bernhardt
*Attorney, Agent, or Firm*—Blair Q. Ferguson; David H. Vance

[57]  ABSTRACT

This invention relates to (2-quinoxalinyloxy) phenoxypropanoic acids, related derivatives thereof, enantiomeric and diastereomeric forms thereof, mixtures of enantiomeric diastereomeric forms thereof, and pharmaceutically acceptable salt forms thereof, pharmaceutical compositions containing them, processes for their preparation, and methods of using them to treat cancer, particularly solid tumors, in mammals.

20 Claims, No Drawings

(2-QUINOXALINYLOXY) PHENOXYPROPANOIC ACIDS AND RELATED DERIVATIVES AS ANTICANCER AGENTS

This is a continuation of application Ser. No. 07/991,525 filed Dec. 15, 1992, now abandoned.

FIELD OF THE INVENTION

This invention relates to (2-quinoxalinyloxy)-phenoxypropanoic acids, related derivatives thereof, enantiomeric and diastereomeric forms thereof, mixtures of enantiomeric and diastereomeric forms thereof, and pharmaceutically acceptable salt forms thereof, pharmaceutical compositions containing them, processes for their preparation, and methods of using them to treat cancer, particularly solid tumors, in mammals.

BACKGROUND OF THE INVENTION

Various quinoxaline derivatives have been reported in the literature to have anticancer activity. Chloroquinoxaline sulfonamide (NSC 339004) has been reported to have antitumor activity [Branda et al., Biochemical Pharmacology, 1988, 37, 4557–4564] and immunosuppressive properties [Branda et al., Biochemical Pharmacology, 1989, 38, 3521–3526], and it has progressed to clinical trials [Rigas et al., Proc. Am. Assoc. Cancer Res., 1990, 31, 177]. A rhodium (I) complex of chloroquinoxaline sulfonamide has also been found to have marginal anticancer activity [Craciunescu et al., An. R. Acad. Farm., 1985, 51, 653–658]. Cytotoxic quinoxaline antibiotics are well known in the literature [Katagiri et al., in Antibiotics, Volume III, Mechanism of Action of Antimicrobial and Antitumor Agents, Corcorn and Hahn, Eds., Springer-Verlag, 1974, pages 234–251, and Waring et al., in Molecular Aspects of Anticancer Drug Action, Neidle and Waring, Eds., Verlag Chemie, 1983, pages 127–156]. Echinomycin (NSC 526417), a quinoxaline antibiotic, is in clinical trials [Foster et al., Invest. New Drugs, 1985, 3, 403–410]. Quinaldopeptin, a quinoxaline antibiotic, exhibited in vitro cytotoxic activity and it prolonged the survival time of mice inoculated with murine P388 leukemia [Toda et al., J. Antibiotics, 1990, 43, 796–808]. BBM 928A (Luzopeptin A), a quinoxaline antitumor antibiotic which is structurally similar to echinomycin, was reported to have activity against various murine tumor model systems [Rose et al. Cancer Res., 1983, 43, 1504–1510]. Several simple bis-quinoxaline analogs of echinomycin have been synthesized, and some of these compounds were reported to be cytotoxic [Piatti et al., An. Quim., Ser. C., 1986, 82, 85–88]. A mono-quinoxaline was reported to be more cytotoxic than the related bis-quinoxalines [Piatti et al., An. Quim., Ser. C., 1989, 85, 105–109]. An indolo[2,3b]-quinoxaline derivative has been reported to have antitumorigenic properties [Zegar et al., Chem. Biol. Interactions, 1989, 72, 277–293]. 5,6-Quinoxalinediones were tested and found not to have significant cytotoxicity against L1210 leukemia [Renault et al., Eur J. Med. Chem., 1981, 16, 545–550].

2-Aryloxypropanoic acid derivatives in general are well known in the literature as herbicidal compounds. (2-Quinoxalinyloxy)phenoxypropanoic acid derivatives, such as Assure®, are well known in the literature as herbicidal agents. Fawzi, U.S. Pat. No. 4,609,396 issued Sep. 2, 1986 disclose among others (2-quinoxalinyloxy) phenoxypropanoic acids and related derivatives as herbicides. Ura et al., U.S. Pat. No. 4,629,493 issued Dec. 16, 1986 also disclose (2-quinoxalinyloxy)phenoxypropanoic acids and related derivatives as herbicides. Serban et al., U.S. Pat. No. 4,803,273 issued Feb. 7, 1989, Serban et al., U.S. Pat. No. 4,655,819 issued Apr. 7, 1987, and Serban et al., EP 0,023,785 A2, issued Feb. 11, 1981, disclose substituted (2-quinoxalinyloxy)phenoxypropanoic acids and related derivatives as herbicides. Davis et al., EP 0,323,727 A2 issued Jul. 12, 1989, disclose substituted (2-quinoxalinyloxy)phenoxypropanoic acids and related derivatives as herbicides.

2-Aryloxypropanoic acid derivatives useful as herbicidal agents may have an asymmetric carbon atom adjacent to the carbonyl group. Various methods to obtain optically active forms of racemic 2-aryloxypropanoic acid derivatives have been disclosed. Nestler et al., U.S. Pat. No. 4,531,969 issued Jul. 30, 1985, and GB 2,042,503 issued Sep. 24, 1990, disclose the synthesis of optically active herbicidal esters from optically active lactate derivatives. Makino et al., EP 0,180,126 issued May 5, 1986, disclose the synthesis of ethyl (D)-(+)-2-[4-(6-chloro-2-quinoxalinyloxy)phenoxy] propionate from an optically active lactate derivative. Kershner et al., EP 0,344,746 issued Jun. 12, 1989 disclose an improved process for the minimization of racemization in the preparation of optically active [(aryloxy)phenoxy] propionate herbicides. Bertola et al., EP 0,299,559 issued Jan. 18, 1989, disclose various micro-organisms which provide for the stereoselective hydrolysis of an aryloxypropanoic acid ester. Russell, U.S. Pat. No. 4,786,732 issued Nov. 22, 1988, discloses the resolution of enantiomers of 2-(4-aryloxyphenoxy)propanoic acids by liquid chromatography with a chiral eluent.

However, there are no literature references which disclose the anticancer utility of (2-quinoxalinyloxy) phenoxypropanoic acids, related derivatives, or pharmaceutical compositions containing these compounds.

The present invention concerns (2-quinoxalinyloxy)-phenoxypropanoic acids, related derivatives thereof, enantiomeric and diastereomeric forms thereof, mixtures of enantiomeric and diastereomeric forms thereof, and pharmaceutically acceptable salt forms thereof, pharmaceutical compositions containing them, processes for their preparation, and methods of using them to treat cancer, particularly solid tumors, in mammals. Some of the compounds of the present invention are known as herbicides, and others are novel. The tumoricidal properties of the known herbicidal compounds of the present invention are unexpected.

DETAILED DESCRIPTION OF THE INVENTION

There is provided by this invention pharmaceutical compositions comprising a compound of formula (ii):

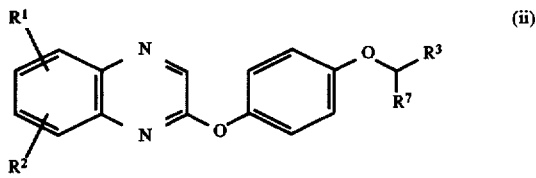

(ii)

and enantiomeric and diastereomeric forms thereof, mixtures of enantiomeric and diastereomeric forms thereof, mixtures of isomers thereof, and pharmaceutically acceptable salt forms thereof, wherein:

$R^1$ and $R^2$ independently are H, F, Cl, Br, $CF_3$, $OCH_3$, or $NO_2$;

$R^3$ is $CO_2H$, $CO_2M$, $CONHCH_2CH_2OH$, $CONHCH_2CH_2CH_2N(CH_3)_2$, $CONHC(CH_2OH)_2CH_3$, $CONR^4R^5$, or $CO_2R^6$;

M is a pharmaceutically acceptable counterion;

$R^4$ and $R^5$ independently are alkyl of 1–4 carbon atoms, cycloalkyl of 5–8 carbon atoms, phenyl, or benzyl;

$R^6$ is alkyl of 1–4 carbon atoms, cycloalkyl of 5–8 carbon atoms, alkenyl or alkynyl of 3–4 carbon atoms, phenyl, or benzyl;

$R^7$ is alkyl of 1–4 carbon atoms.

Preferred pharmaceutical compositions of the present invention comprise compounds of formula (ii) wherein:

$R^1$ and $R^2$ independently are H, F, Cl, Br, $CF_3$, $OCH_3$, or $NO_2$;

$R^3$ is $CO_2H$, $CO_2M$, $CONHCH_2CH_2OH$, $CONHCH_2CH_2CH_2N(CH_3)_2$, $CONHC(CH_2OH)_2CH_3$, $CONR^4R^5$, or $CO_2R^6$;

M is a pharmaceutically acceptable counterion;

$R^4$ and $R^5$ independently are alkyl of 1–4 carbon atoms, cycloalkyl of 5–8 carbon atoms, phenyl, or benzyl;

$R^6$ is alkyl of 1–4 carbon atoms, cycloalkyl of 5–8 carbon atoms, alkenyl or alkynyl of 3–4 carbon atoms, phenyl, or benzyl; and $R^7$ is $CH_3$.

Further preferred pharmaceutical compositions of the present invention comprise compounds of formula (ii) wherein:

$R^1$ is 7-Cl, 7-Br, or 6-Cl;

$R^2$ is H;

$R^3$ is $CO_2CH_3$, $CO_2M$, $CONHCH_2CH_2OH$, $CONHCH_2CH_2CH_2N(CH_3)_2$, $CON(CH_3)_2$, $CONHC(CH_2OH)_2CH_3$;

M is Na, K, Li, $NH_4$, $MeNH_3$, or $Me_2NH_2$;

$R^7$ is $CH_3$.

Specifically preferred pharmaceutical compositions of the present invention comprise compounds of formula (ii) wherein:

$R^1$ is 7-Cl, $R^2$ is H, $R^3$ is $CO_2CH_3$, $R^7$ is $CH_3$, (racemic);
$R^1$ is 7-Cl, $R^2$ is H, $R^3$ is $CO_2CH_3$, $R^7$ is $CH_3$, (R);
$R^1$ is 7-Cl, $R^2$ is H, $R^3$ is $CO_2CH_3$, $R^7$ is $CH_3$, (S);
$R^1$ is 7-Cl, $R^2$ is H, $R^3$ is $CO_2Na$, $R^7$ is $CH_3$, (R);
$R^1$ is 7-Cl, $R^2$ is H, $R^3$ is $CO_2Na$, $R^7$ is $CH_3$, (S);
$R^1$ is 7-Cl, $R^2$ is H, $R^3$ is $CO_2Na$, $R^7$ is $CH_3$, (racemic);
$R^1$ is 7-Br, $R^2$ is H, $R^3$ is $CONHCH_2CH_2OH$, $R^7$ is $CH_3$;
$R^1$ is 7-Br, $R^2$ is H, $R^3$ is $CONHCH_2CH_2CH_2N(CH_3)_2$, $R^7$ is $CH_3$;
$R^1$ is 7-Br, $R^2$ is H, $R^3$ is $CONHC(CH_2OH)_2CH_3$, $R^7$ is $CH_3$.

There is also provided by this invention 2-phenoxyquinoxaline compounds of formula (i), enantiomeric forms thereof, mixtures of enantiomeric forms thereof, mixtures of isomers thereof, and pharmaceutically acceptable salt forms thereof, wherein:

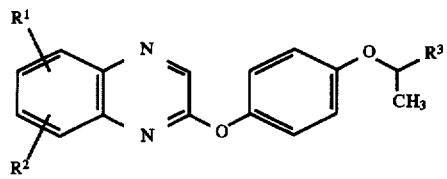

$R^1$ is 7-Cl or 7-Br;

$R^2$ is H;

$R^3$ is $CO_2CH_3$, $CO_2M$, $CONHCH_2CH_2OH$, $CONHCH_2CH_2CH_2N(CH_3)_2$, or $CONHC(CH_2OH)_2CH_3$;

M is Na or K;

with the proviso that when $R^3$ is $CO_2CH_3$ said mixture is not racemic.

Specifically preferred compounds of the present invention include the compounds of formula (i) wherein:

$R^1$ is 7-Cl, $R^2$ is H, $R^3$ is $CO_2CH_3$, (R);
$R^1$ is 7-Cl, $R^2$ is H, $R^3$ is $CO_2CH_3$, (S);
$R^1$ is 7-Cl, $R^2$ is H, $R^3$ is $CO_2Na$, (R);
$R^1$ is 7-Cl, $R^2$ is H, $R^3$ is $CO_2Na$, (S);
$R^1$ is 7-Cl, $R^2$ is H, $R^3$ is $CO_2Na$, (racemic);
$R^1$ is 7-Br, $R^2$ is H, $R^3$ is $CONHCH_2CH_2OH$;
$R^1$ is 7-Br, $R^2$ is H, $R^3$ is $CONHCH_2CH_2CH_2N(CH_3)_2$;
$R^1$ is 7-Br, $R^2$ is H, $R^3$ is $CONHC(CH_2OH)_2CH_3$.

There is also provided by this invention methods of treating cancer in a mammal, including leukemia and solid tumors, including pancreatic, mammary, colon, and melanoma tumors, comprising the administration to a mammal bearing such a tumor a therapeutically effective tumor-inhibiting amount of a compound of formula (ii) or (i) as described above.

The compounds herein described may have asymmetric centers. All chiral, diastereomeric, and racemic forms are included in the present invention. All chiral, diastereomeric, and racemic forms are intended for a given compound unless the specific stereochemistry for the compound is specifically indicated. Combinations of substituents and/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like. "Halo" as used herein refers to fluoro, chloro, bromo, and iodo; and "counterion" is used to represent a small, negatively charged species such as chloride, bromide, hydroxide, acetate, sulfate, and the like, or, as appropriate, a small positively charged species such as, but not limited to, Na, K, Li, $NH_4$, $MeNH_3$, or $Me_2NH_2$.

As used herein, "aryl" or "aromatic residue" is intended to mean phenyl or naphthyl; "carbocyclic" is intended to mean any stable 5- to 7-membered monocyclic or bicyclic or 7- to 14-membered bicyclic or tricyclic carbon ring, any of which may be saturated, partially unsaturated, or aromatic, for example, indanyl or tetrahydronaphthyl (tetralin).

The term "substituted", as used herein, means that any one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Synthesis

Compounds of the present invention can be synthesized using the methods described below, together with synthetic methods known in the art of synthetic organic chemistry. The references cited below are all incorporated herein by reference.

The synthesis of some of the known compounds of the present invention of formula (i) is described in Fawzi, U.S. Pat. No. 4,609,396, Ura et al., U.S. Pat. No. 4,629,493, and Serban et al., U.S. Pat. No. 4,803,273. Furthermore, the methods disclosed in these patents can be adapted to the synthesis of known or novel compounds of formula (i) by one skilled in the art.

The synthesis generally involves the reaction of a 2-chloroquinoxaline (1) with a 2-(4-hydroxyphenoxy) propanoate (2) as shown in Scheme I. One method disclosed in Fawzi, et al. involves the reaction of a 2-chloroquinoxaline (1) with an alkali metal salt of a 2-(4-hydroxyphenoxy)propanoate. Suitable solvents for the reaction include dimethylformamide, dimethylsulfoxide, diglyme, and methylethylketone. The reaction is preferably conducted at a temperature between about 25° C. and about 130° C. Alternatively, a 2-chloroquinoxaline (1) can be reacted with a 2(4-hydroxyphenoxy)propanoate (2) in the presence of a heterogeneous base, such as potassium carbonate, in a solvent such as acetone or dimethylformamide, at a temperature between about 25° C. and the boiling temperature of the solvent.

Scheme I:

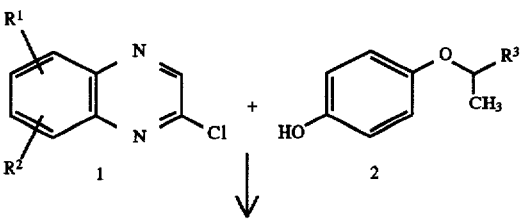

Scheme I:
-continued

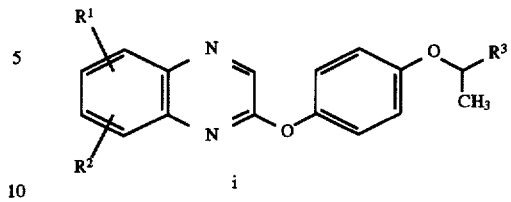

The 2-chloroquinoxalines (1) used in the preparation of compounds of formula (i) can be prepared by methods known in the art. For example, glyoxylic acid is reacted with a substituted o-phenylenediamine (3) in a polar solvent such as ethanol or isopropanol to afford a quinoxalin-2-ol (4) as shown in Scheme II. Depending on the substitution pattern, a isomeric mixture of quinoxalin-2-ol products may result from this reaction. An isomer mixture may be separated into pure isomers by methods such as recrystallization, HPLC methods, and other methods well known to those skilled in the art. For example, the Japanese patent application JP 58,15,963 (Jul. 21, 1981) reports the separation of a mixture of 6-chloroquinoxalin-2-ol and 7-chloroquinoxalin-2-ol isomers by treatment with dimethylformamide. Alternatively, an isomeric mixture may be purified at a later stage in the synthesis.

The quinoxalin-2-ol (4) can be converted to a 2-chloroquinoxaline (1) by reacting it with a chlorinating reagent such as phosphorous oxychloride. Alternatively, (4) can be brominated or tosylated to provide an equivalent reagent to (1) for the reaction with (2) to provide compounds of formula (i). A mixture of 2-chloroquinoxaline isomers may be separated into pure isomers by methods such as recrystallization, HPLC methods, and other methods well known to those skilled in the art.

Scheme II:

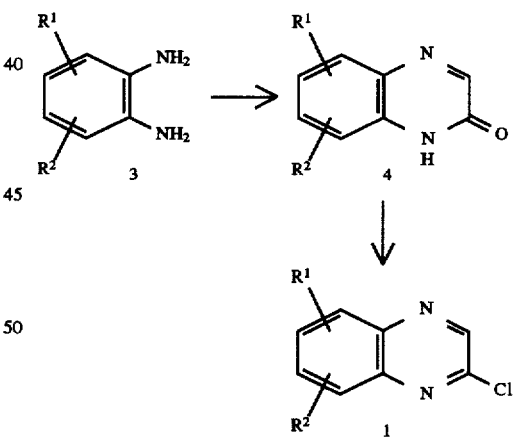

The 2-(4-hydroxyphenoxy)propanoate compounds (2) of the present invention can be prepared by well known methods as shown in Scheme III. Compounds of formula (2) wherein $R^3$ is an ester group can be prepared by reacting (5) with $R^3CH(CH_3)X$, wherein X is a leaving group such as Br or tosylate, to provide (6) as shown in Scheme III. The benzyl protecting group of (6) is easily removed by standard deprotection conditions such as catalytic hydrogenation to provide compounds of formula (2) wherein $R^3$ is an ester group.

The compounds of formula (2) wherein $R^3$ is an ester group can be transaminated to afford compounds of formula (2) wherein R³ is an amide by reacting it with a suitable amine such as R'R"NH, preferably using the amine as solvent and reagent at a temperature up to the boiling point of the solvent. Alternatively, the compounds of formula (2) wherein R³ is an ester can be converted to compounds of formula (2) wherein R³ is an amide by methods well known to those skilled in the art. The compounds of formula (2) wherein R³ is an amide can be converted into compounds of formula (i) wherein R³ is an amide by reacting it with the compounds of formula (1) as described in Scheme I.

Scheme III:

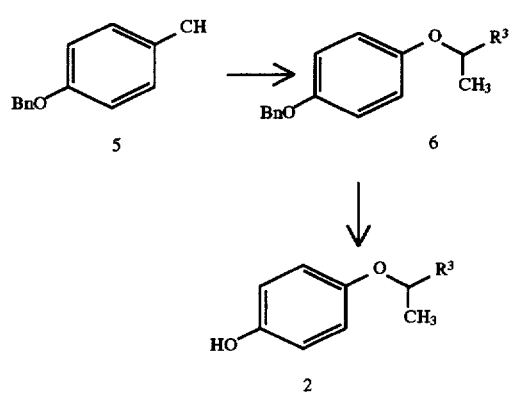

Compounds of formula (i) wherein R³ is an ester group are useful starting materials for other compounds of the present invention as shown in Scheme IV. Compounds of formula (8) can be prepared by the hydrolysis of the ester group of (7) under standard conditions. The acids of formula (8) can be converted to pharmaceutically acceptable carboxylic acid salts by procedures well known to those skilled in the art. The carboxylic acids of formula (8) can be reacted with a chlorinating agent such as phosphorous oxychloride and then reacted with a suitable amine R'R"NH to provide the amides of formula (9).

Scheme IV:

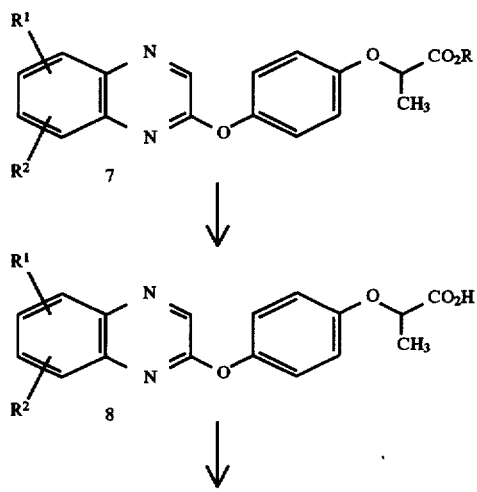

-continued
Scheme IV:

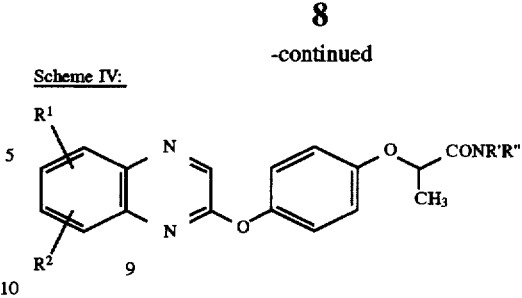

Optically active compounds of the present invention may be prepared through the use of optically active starting materials as shown in Scheme V. The sodium metal salt of (5) can be reacted with an optically active tosylate followed by a catalytic reduction, for example by Pd/C under hydrogen, to afford the optically active compound (10). Either enantiomer of the tosylate is readily prepared by known methods from the commercially available methyl (R)-(+) lactate or methyl (S)-(-) lactate. Optically active compound (11) can be prepared from (10) as described above. Additionally, the methods described in Nestler et al., U.S. Pat. No. 4,531,969, Makino et al., EP 0,180,126, Kershner et al., EP 0,344,746, Bertola et al., EP 0,299,559, and Russell, U.S. Pat. No. 4,786,732, may be adapted by one skilled in the art for use in the synthesis of optically active compounds of the present invention.

Scheme V:

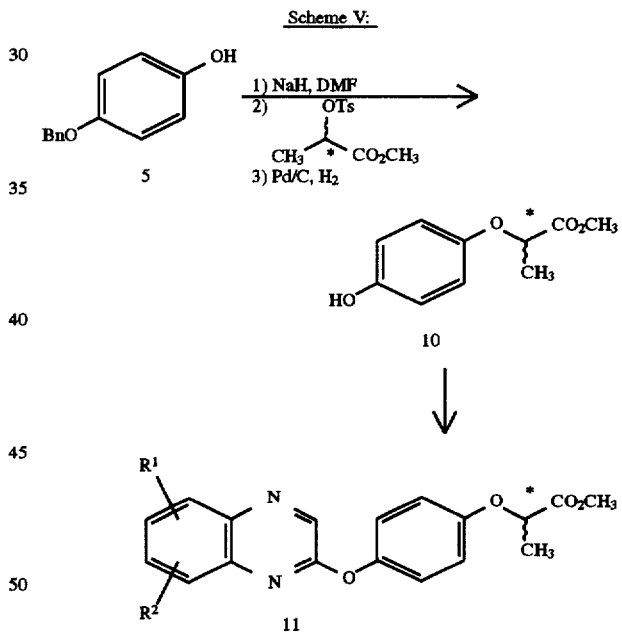

The compounds of formula (ii) may be synthesized using methods analogous to those described above for compounds of formula (i).

The compounds of this invention can be further understood by the following examples, which do not constitute a limitation of the invention.

Preparation of 2,7-Dichloroquinoxaline

Part A.

A solution of 4-chloro-1,2-phenylenediamine (200 g, 1.403 mole) in isopropanol (1300 mL) was stirred under nitrogen at room temperature and glyoxylic acid monohydrate (200 g, 2.71 mole) was added in two portions. The reaction was stirred overnight then cooled to 10° C. The purple precipitate was collected by filtration, washed with cold isopropanol and hexane, and dried under high vacuum to afford a mixture of 6-chloroquinoxalin-2-ol and 7-chloroquinoxalin-2-ol (228 g, 89.6% yield) as a solid: mp 256°–260° C.

Part B.

A solution of the product of Part A (228 g, 1.263 mole) and phosphorous oxychloride (1070 mL) was heated to reflux under nitrogen for two hours. Approximately 600–700 mL of $POCl_3$ was removed by distillation, toluene was added, and the mixture was further distilled. The reaction was then cooled to 0° C. and water (1 L) and water (700 mL) were added. The reaction was basified with solid potassium carbonate and water and ether were added as needed to maintain solubility. Ethyl acetate (2 L) was added and the organic layer was separated. The water layer was extracted with ether and ethyl acetate then the organic layers were combined and extracted with water (3×1 L) and brine (2×1 L) and dried over $MgSO_4$, $Na_2SO_4$, filtered through floricil, $MgSO_4$ and celite, and evaporated to afford a 70:30 mixture of 2,6-dichloroquinoxaline to 2,7-dichloroquinoxaline (182 g, 72% yield) as a beige solid: mp 131°–133° C. The isomers can be separated by careful flash chromatography or by HPLC.

The 2,6- and 2,7-dichloroquinoxaline are characterized respectively with a HPLC retention time of 3.3 minutes for the 2,6-isomer and 3.8 minutes for the 2,7-isomer, using the following conditions: column; silica gel, five micron particles with sixty angstrom pore; solvent; 5% dimethoxyethane in hexane; flow rate; 1.5 mL/min; detection; 265 nanometers (UV).

The isolation of pure isomers can be accomplished in three steps. First, the crude mixture (30 grams) is passed through a Waters PrePak silica cartridge, 47 mm I.D.×300 mm long, using methylene chloride at 40 mL/min with detection at 300 nm (UV), the mixture is fractionated with early impurities eluting at 30 minutes, the isomeric mixture eluting from 30 to 60 minutes and highly retained material remaining on the cartridge. The second step is to isolate the target 2,7-dichloroquinoxaline and increase its concentration to 97% by injecting 150 mgs onto a preparative silica column, 50 mm I.D.×250 mm long. The amount injected will vary depending on the 2,7-isomer content. The sample is dissolved in n-butyl chloride and is injected to a mobile phase of 2.5% dimethoxyethane in 97.5% hexane. The third step is to recycle the target isomer under the same conditions. This procedure produced 2,7-dichloroquinoxaline of >99% purity. mp 141°–142° C. $_1$H NMR (CDCl$_3$) δ8.77 (s, 1H), 8.06 (d, J=9 Hz, 1H), 8.02 (d, J=2 Hz, 1H), 7.73 (dd, J=9 Hz, J=2 Hz, 1H). MS m/e 199 (M$^+$+H). Anal Calcd for $C_8H_4N_2Cl_2$: C, 48.28; H, 2.03; N, 14.07. Found: C, 48.32; H, 1.92; N, 14.01.

EXAMPLE 3

Racemic Methyl 2-[4-(7-chloroquinoxalinyloxy)phenoxy]propionate

A mixture of 2,7-dichloroquinoxaline (2.8 g, 14.1 mmol), methyl 2-(4-hydroxyphenoxy)propanoate (2.76 g, 14.1 mmol), and pulverized potassium carbonate (3.9 g, 28.2 mmol) in acetone (70 mL) was refluxed for 3 hours. The reaction mixture was cooled to room temperature and methylene chloride and water were added to the reaction mixture. The organic phase was removed, and the aqueous phase was extracted with methylene chloride. The combined organic phase was washed with water, dried over potassium carbonate, concentrated, and dried under high vacuum. The product was purified by flash chromatography with 6:1 petroleum ether:ethyl ether to afford the desired product (2.8 g, 55% yield) as a solid: mp 103° C.; MS m/e 359 (M$^+$+H). Anal. Calcd for $C_{18}H_{15}ClN_2O_4$: C, 60.26; H, 4.21; N, 7.81; Cl, 9.88. Found: C, 60.44, H, 4.31; N, 7.69, Cl, 9.98.

EXAMPLE 8

Racemic Sodium 2-[4-(7-chloroquinoxalinyloxy)phenoxy]propionate

Part A.

A solution of racemic methyl 2-[4-(7-chloroquinoxalinyloxy)phenoxy]propionate (3.0 g, 8.36 mmol) in THF (30 mL) and water (6 mL) with potassium hydroxide (3 eq, 25.1 mmol, 1.4 g) was stirred at room temperature overnight. Water was added and the mixture was acidified to pH=1 with 1N HCl. The mixture was extracted with $CH_2Cl_2$ (2×50 mL), dried over $Na_2SO_4$ and evaporated to afford an oily yellow solid, which was triturated in EtOAc to afford the corresponding carboxylic acid (0.855 g, 30% yield) as a white powder: mp 172°–174° C.; $^1$H NMR (DMSO d$_6$) δ13.12 (br s, 1H), 8.86 (s, 1H), 8.07 (d, J=9 Hz, 1H), 7.82 (d, J=2 Hz, 1H), 7.71 (dd, J=2 Hz, J=9 Hz, 1H), 7.26 (m, 2H), 6.96 (m, 2H), 4.87 (q, J=7 Hz, 1H), 1.54 (d, J=7 Hz, 3H); MS m/e (M$^{++H}$) 345, (M$^{++NH}_4$) 362; HRMS calcd for $C_{17}H_{13}N_2O_4Cl$ 345.0642, found 345.0648. Anal Calcd for $C_{17}H_{13}N_2O_4Cl$: C, 59.23; H, 3.80; N, 8.13. Found: C, 59.01; H, 3.74; N, 7.95.

Part B.

The product of Part A (0.50 g, 1.45 mmol) was gently warmed in a solution of 0.1N NaOH (14.5 mL, 1.45 mmol) and water (15 mL) for 20 minutes until all of the product of Part A was dissolved and the pH was neutral. The reaction mixture was evaporated to dryness under high vacuum to afford racemic sodium 2-[4-(7-chloroquinoxalinyloxy)phenoxy]propionate (0.509 g, 96% yield) as a white crystalline solid: mp 129°–131° C.; $^1$H NMR (DMSO d$_6$) δ8.83 (s, 1H), 8.06 (d, J=8 Hz, 1H), 7.84 (d, J=2 Hz, 1H), 7.69 (dd, J=2 Hz, J=9 Hz, 1H), 7.14 (m, 2H), 6.86 (m, 2H), 4.25 (q, J=7 Hz, 1H), 1.39 (d, J=7 Hz, 3H); MS m/e (M$^+$+H—Na) 345; HRMS calcd for $C_{17}H_{13}N_2O_4Cl$ (M$^+$+H—Na) 345.0642, found 345.0644. Anal Calcd for $C_{17}H_{12}N_2O_4ClNa.H_2O$: C, 53.07; H, 3.67; N, 7.28. Found C, 52.98; H, 3.56; N, 7.06.

EXAMPLE 18

Part A.

A solution of methyl 2-(4-hydroxyphenoxy)propanoate (5.0 g, 25.5 mmol) and ethanolamine (3.08 mL, 51.0 mmol) was refluxed overnight. A TLC (95:5 $CH_2Cl_2$/MeOH) showed the reaction was complete. The reaction mixture was cooled and diluted with a small amount of $CH_2Cl_2$ and poured directly onto a silica gel column for purification. The column was eluted with 95: 5 $CH_2Cl_2$/MeOH then 9: 1. The product was collected and evaporated to dryness under high vacuum. A light yellow oil (4.755 g, 83% yield) resulted. $^1$H NMR (DMSO d$_6$) δ8.80 (br, 1H), 7.70–7.62 (m, 1H), 6.85–6.70 (m, 2H, 6.70–6.52 (m, 2H), 4.60 (br, 1H), 4.47 (q, J=7 Hz, 1H), 3.54–3.47 (m, 2H), 3.37–3.27 (m, 2H), 1.42 (d, J=7 Hz, 3H). MS m/e (M$^+$+H) 226.

Part B.

A mixture of the product of Part A (1.25 g, 5.55 mmol), 2-chloro-7-bromoquinoxaline (1.35 g, 5.55 mmol), and potassium carbonate (1.53 g, 11.1 mmol) in acetone (20 mL) was refluxed for 5 hr. Water (50 mL) and $CH_2Cl_2$ were added and then extracted with $CH_2Cl_2$ (3×50 mL). The organic layer was washed with water (3×25 mL), dried over $Na_2SO_4$, and evaporated to dryness. This residue was triturated in 1:1:1 ethyl ether:petroleum ether:ethyl acetate and the product was collected by filtration and dried under vacuum. A slightly off-white solid (1.392 g, 58% yield) was recovered: mp 147°–148° C. $^1$H NMR ($CDCl_3$) $\delta$8.68 (s, 1H), 7.95–7.87 (m, 2H), 7.72–7.65 (m, 1H), 7.20–7.10 (m, 2H), 7.03–6.93 (m, 2H), 6.88 (br, 1H), 4.74 (q, J=7 Hz, 1H), 3.80–3.62 (m, 2H) 3.62–3.50 3.50 (m, 1H), 3.48–3.35 (m, 1H), 2.52 (br, 1H), 1.64 (d, J=7 Hz, 3H). HRMS $C_{19}H_{18}N_3O_4Br$: calc 431.0481; found 431.0478. Anal Calcd for $C_{19}H_{18}N_3O_4Br$: C, 52.79; H, 4.20; N, 9.72. Found: C, 52.39; H, 4.10; N, 9.46.

EXAMPLE 20

Part A.

A neat solution of methyl 2-(4-hydroxyphenoxy)propanoate (5.0 g, 25.5 mmol) and 3-dimethylaminopropylamine (5.21 g, 51.0 mmol) was refluxed overnight. The mixture was cooled, diluted with a small amount of $CH_2Cl_2$ and poured directly onto a silica gel column. The column was eluted with $CH_2Cl_2$, then $CH_2Cl_2$/MeOH mixtures. The product fractions were concentrated to afford a brown oil, which was used immediately.

Part B.

A mixture of the product of Part A (1.50 g, 5.63 mmol), 2-chloro-7-bromoquinoxaline (1.37 g 5.63 mmol), pulverized potassium carbonate (1.56 g, 11.26 mmol) and acetone (20 mL) was refluxed for 5 hr then stirred at room temperature overnight. Water and $CH_2Cl_2$ were added and the water layer was extracted with $CH_2Cl_2$. The combined organic layers were extracted with water, dried over $Na_2SO_4$ and evaporated to afford a solid. This was purified by silica gel chromatography with $CH_2Cl_2$/MeOH as the eluent to afford the product (0.764 g, 29% yield) as a light tan solid: mp 109°–111° C. $^1$H NMR ($CDCl_3$) $\delta$8.67 (s, 1H), 7.95–7.87 (m, 2H), 7.87–7.80 (m, 1H), 7.76 (dd, J=2 Hz, 9 Hz, 1H), 7.20–7.15 (m, 2H), 7.02–6.95 (m, 2H), 4.68 (q, J=7 Hz, 1H), 3.50–3.37 (m, 2H), 2.55–2.43 (m, 2H), 2.30 (s, 6H), 1.82–1.70 (m, 2H), 1.61 (d, J=7 Hz, 3H); MS m/e ($M^++H$) 475, Br pattern; HRMS calcd for $C_{22}H_{25}N_4O_3Br$ 473.1188, found 474.1181.

EXAMPLE 21

Part A.

A neat solution of methyl 2-(4-hydroxyphenoxy)propanoate (10.0 g, 51.0 mmol) and 2-amino-2-methyl-1,3-propanediol (10.72 g, 102 mmol) was refluxed overnight. The mixture was cooled, diluted with a small amount of $CH_2Cl_2$ and poured directly onto a silica gel column and eluted first with $CH_2Cl_2$, then 9:1 $CH_2Cl_2$/MeOH. The crude product was chromatographed again ($CH_2Cl_2$, then $CH_2Cl_2$:EtOAc) to afford the desired product (5.682 g, 41% yield) as a yellowish oil. $^1$H NMR (DMSO $d_6$) $\delta$8.99 (s, 1H), 7.16 (s, 1H), 6.80–6.70 (m, 2H), 6.68–6.60 (m, 2H), 4.82 (m, 2H), 4.43 (q, J=7 Hz, 1H), 3.53–3.40 (m, 2H), 3.40–3.27 (m, 2H), 1.33 (d, J=7 Hz, 3H), 1.14 (s, 3H); MS m/e ($M^++H$) 270.

Part B.

A mixture of the product of Part A (5.0 g, 18.6 mmol), 2-chloro-7-bromoquinoxaline (4.52 g, 18.6 mmol), pulverized potassium carbonate (5.13 g, 37.2 mmol) and acetone (100 mL) was refluxed for 5 hr then stirred overnight at room temperature. Water and $CH_2Cl_2$ were added and the water layer was extracted with $CH_2Cl_2$. The combined organic layers were extracted with water, dried over $Na_2SO_4$ and evaporated to dryness. This was purified by silica gel column chromatography with EtOAc, EtOAc/$CH_2Cl_2$ then EtOAc/$CH_2Cl_2$/MeOH as the eluents. The crude product was chromatographed again under the same conditions to afford the product (0.71 g, 8% yield) as a light yellow solid: mp 44°–45° C. $^1$H NMR ($CDCl_3$) $\delta$8.69 (s, 1H), 7.93–7.88 (m, 2H), 7.68 (dd, J=2 Hz, 9 Hz, 1H), 7.20 (m, 2H), 7.00 (m, 2H), 6.88 (s, 1H), 4.70 (q, J=7 Hz, 1H), 3.83–3.75 (m, 1H), 3.74–3.55 (m, 4H), 3.53–3.47 (m, 1H), 1.64 (d, J=6 Hz, 3H), 1.23 (s, 3H); MS m/e ($M^++H$) 478; HRMS calc for $C_{21}H_{22}N_3O_4Br$ 478.0800, found 478.0811. Anal Calcd for $C_{21}H_{22}N_3O_4Br$: C, 52.95; H, 4.66; N, 8.64. Found: C, 52.97; H, 4.73; N, 8.64.

EXAMPLE 31

Methyl (R)-(+)2-[4-(7-chloroquinoxalinyloxy)phenoxy]propionate

Part A.

Methyl (S)-(-) lactate (5.0 g, 48.03 mmol) was dissolved in $CH_2Cl_2$ (15 mL) with triethylamine (10 mL). Tosyl chloride (10.0 g, 52.45 mmol) was added and the mixture was stirred at 0° C., followed by TLC (4:1 hexane. EtOAc; Rf 0.25). The reaction was slowly warmed to room temperature and more lactate was added in small portions (4.34 g total) until the reaction was complete. After about 2 hours, ether (50 mL) was added and the mixture was extracted with 1N HCl, saturated NaCl, dried over $Na_2SO_4$, and evaporated to afford the corresponding (S)-(-) tosylate as a pale yellow oil: (11.4 g, 84% yield). $^1$H NMR ($CDCl_3$) $\delta$7.83 (d, J=8.5 Hz, 2H), 7.35 (d, J=8.3 Hz, 2H), 4.96 (q, J=7 Hz, 1H), 3.67 (s, 3H), 2.46 (s, 3H), 1.51 (d, J=7 Hz, 3H); $[\alpha]_D^{25}$ =–35.13° (c, 0.612, $HCCl_3$).

Part B.

A flask was charged with sodium hydride (60% in oil, 6.0 g, 0.15 mole) which was washed with hexane to remove the oil. DMF (120 mL) was added and the mixture was cooled to 0° C. A solution of p-benzyloxyphenol (32 g, 0.16 mole) in DMF (120 mL) was added dropwise over 30 minutes and the reaction was stirred at 0° C. for 30 minutes then warmed to room temperature. A solution of the product of Part A (29.0 g, 0.11 mole) in DMF (80 mL) was added over 20 minutes. After 90 minutes, ether and saturated ammonium chloride were added and the aqueous phase was extracted with ether. The ether layer was washed with water, brine, dried over $MgSO_4$ and magnesol, and filtered through $MgSO_4$, celite and florisil, to give a clear water white filtrate which was evaporated to give a waxy white solid (38.0 g). This was triturated in hexane and the white precipitate, unreacted phenol, was removed by filtration. The filtrate was evaporated and purified further by column chromatography (silica gel, 85:15 hexane:EtOAc then 80:20; Rf 0.48) to afford methyl (R)-(+) 2-(4-benzyloxyphenoxy)propanoate (27.0 g, 84.5% yield) as a solid: mp 63°–65° C.; $^1$H NMR ($CDCl_3$) $\delta$7.17 (m, 5H), 6.70–6.93 (m, 4H), 5.0 (s, 2H), 4.67 (q, J=7 Hz, 1H), 3.75 (s, 3H), 1.59 (d, J=7 Hz, 3H).

Part C.

A solution of the product of Part B (27.0 g, 0.095 moles), ethyl acetate (215 mL), conc HCl (12 drops) and Pd/C (1.7 g) was shaken on a Parr hydrogenator for 3.5 hours, after which TLC (60:40 hexane/EtOAc; Rf 0.36) indicated the reaction was complete. The mixture was filtered through celite, washed with EtOAc, and evaporated to an amber oil. The oil was dissolved in EtOAc, dried over $MgSO_4$, filtered through celite and $MgSO_4$, and evaporated to a clear filtrate and dried under high vacuum to afford methyl (R)-(+) 2-(4-hydroxyphenoxy)propanoate (18.5 g, 100% yield). A mixture of methyl (R)-(+) 2-(4-hydroxyphenoxy)propanoate (18.5 g, 0.094 moles), 2,7-dichloroquinoxaline (14.5 g, 0.073 mole), and powdered potassium carbonate (13.3 g, 0.964 mole) in dry acetone (170 mL) was refluxed overnight. When a TLC showed the reaction was complete (Rf 0.30, 1:1 hexane:EtOAc), the mixture was filtered and washed with acetone, dried with $MgSO_4$, and evaporated to dryness to a beige solid. This was purified by several silica gel columns (80:20 hexane:EtOAc, then 75:25 hexane:EtOAc) to obtain a fluffy white solid which was recrystallized repeatedly from hexane to afford methyl (R)-(+) 2-[4-(7-chloroquinoxalinyloxy)phenoxy]propionate as a solid: mp 80° C. $^1$H NMR ($CDCl_3$) δ8.65 (s), 7.97 (d, J=9 Hz, 1H), 7.75 (d, J=2 Hz, 1H), 7.54 (dd, J=2 Hz, 9 Hz, 1H), 7.18 (m, 2H), 6.95 (m, 2H), 4.80 (q, J=7 Hz, 1H), 3.80 (s, 3H), 1.66 (d, J=7 Hz, 3H). $[\alpha]_D^{25}$=+40.43. MS calc 358.78, found 358.78. Anal Calcd for $C_{18}H_{15}N_2O_4Cl$: C, 60.26; H, 4.21; N, 7.81. Found: C, 60.16; H, 4.10; N, 7.68.

EXAMPLE 32

Preparation of methyl (S)-(−) 2-[4-(7-chloroquinoxalinyloxy)phenoxy]propionate.

The procedure of Example 31 was used with methyl (R)-(+) lactate as the starting material. The product was recovered as a white solid: mp 78.6°–79.2° C. $^1$H NMR ($CDCl_3$) δ8.64 (s, 1H), 7.97 (d, J=9 Hz, 1H), 7.75 (d, J=2 Hz, 1H), 7.54 (dd, J=2 Hz, 9 Hz, 1H), 7.18 (m, 2H), 6.95 (m, 2H), 4.79 (q, J=7 Hz, 1H), 3.80 (s, 3H), 1.66 (d, J=7 Hz, 3H); $[\alpha]_D^{25}$=−36.59° (c=0.604 mg/ml, $HCCl_3$).

EXAMPLE 33

(R)-(+) sodium 2-[4-(7-chloroquinoxalinyloxy)phenoxy]propionate

The procedure of Example 8 was used with methyl (R)-(+) 2-[4-(7-chloroquinoxalinyloxy)phenoxy]propionate as the starting material. The product was recovered as a white solid: mp 232° C. $^1$H NMR (DMSO $d_6$) δ8.83 (s, 1H), 8.06 (d, J=9 Hz, 1H), 7.84 (d, J=2 Hz, 1H), 7.69 (dd, J=2 Hz, 9 Jz, 1H), 7.14 (m, 2H), 6.86 (m, 2H), 4.25 (q, J=7 Hz, 1H), 1.38 (d, J=7 Hz, 3H); MS m/e ($M^+$+H-Na) 345; $[\alpha]_D^{25}$=+22.59° (c=0.602 mg/ml, $H_2O$). Anal Calcd for $C_{17}H_{12}N_2O_4ClNa \cdot H_2O$: C, 53.07; H, 3.67; N, 7.28. Found: C, 52.71; H, 3.40; N, 7.20.

EXAMPLE 34

(S)-(−) sodium 2-[4-(7-chloroquinoxalinyloxy)phenoxy]propionate

Part A.

The product of Example 8, Part A was separated by HPLC on a chiral OD column using a solution of 0.1% TFA, 20% isopropanol, and 79.9% hexane as the eluent into a (+)-isomer: mp=199°–200° C.; $[\alpha]_D^{25}$=+27.91 (c=0.602, DMSO); and a (−)-isomer: mp=202°–203° C.; $[\alpha]_D^{25}$=−28.57 (c=0.602, DMSO); $^1$H NMR (DMSO $d_6$) δ13.10 (br s, 1H), 8.85 (s, 1H), 8.07 (d, J=9 Hz, 1H), 7.82 (d, J=2 Hz, 1H), 7.70 (dd, J=2 Hz, 9 Hz, 1H), 7.25 (m, 2H), 6.96 (m, 2H), 4.86 (q, J=7 Hz, 1H), 1.53 (d, J=7 Hz, 3H); MS m/e ($M^+$+H-Na) 345; HRMS calcd for $C_{17}H_{13}N_2O_4Cl$: C, 59.23; H, 3.80; N, 8.13. Found C, 58.94; H, 3.77; N, 7.91.

Part B.

The procedure of Example 8, Part B was used with the (−)-isomer product of Part A as the starting material. This procedure gave (S)-(−) sodium 2-[4-(7-chloroquinoxalinyloxy)phenoxy]propionate as a white solid: mp 234°–235° C. $^1$H NMR (DMSO $d_6$) δ8.83 (s, 1H), 8.06 (d, J=9 Hz, 1H), 7.87 (d, J=2 Hz, 1H), 7.69 (dd, J=2 Hz, 9 Hz, 1H), 7.14 (m, 2H), 6.85 (m, 2H), 4.23 (q, J=7 Hz, 1H), 1.37 (d, J=7 Hz, 3H); MS m/e ($M^+$+H-Na) 345; HRMS calcd for $C_{17}H_{14}N_2O_4Cl$ ($M^+$+H-Na) 345.0642, found 345.0629; $[\alpha]_D^{25}$=−22.76 (c=0.602 mg/ml, $H_2O$). Anal. Calcd for $C_{17}H_{12}N_2O_4ClNa \cdot H_2O$: C, 53.07; H, 3.67; N, 7.28. Found: C, 52.70; H, 3.48; N, 7.09.

TABLE 1

Racemic Compounds of Formula (i)

| Example | $R^1$ | $R^2$ | $R^3$ | mp (°C.) |
|---|---|---|---|---|
| 1 | 7-F | H | $CO_2CH_3$ | |
| 2 | 7-F | H | $CO_2CH_2CH_3$ | |
| 3 | 7-Cl | H | $CO_2CH_3$ | 103 |
| 4 | 7-Cl | H | $CO_2CH_2CH_3$ | |
| 5 | 7-Br | H | $CO_2CH_3$ | 93–95 |
| 6 | 7-Br | H | $CO_2CH_2CH_3$ | |
| 7 | 7-F | H | $CO_2Na$ | |
| 8 | 7-Cl | H | $CO_2Na$ | 129–131 |
| 9 | 7-Cl | H | $CO_2K$ | |
| 10 | 7-Cl | H | $CO_2Li$ | |
| 11 | 7-Br | H | $CO_2Na$ | |
| 12 | 7-Br | H | $CO_2K$ | |
| 13 | 7-Br | H | $CO_2H$ | 176–178 |
| 14 | 7-Br | H | $CO_2NH_4$ | |
| 15 | 6-Cl | 7-Cl | $CO_2CH_2C_6H_5$ | |
| 16 | 6-Cl | 7-Cl | $CO_2CH_2CH=CH_2$ | |
| 17 | 7-Cl | H | $CONH(CH_2)_2OH$ | |
| 18 | 7-Br | H | $CONH(CH_2)_2OH$ | 147–148 |
| 19 | 7-F | H | $CONH(CH_2)_2OH$ | |
| 20 | 7-Br | H | $CONH(CH_2)_3N(CH_3)_2$ | 109–111 |
| 21 | 7-Br | H | $CONHC(CH_2OH)_2CH_3$ | 44–45 |
| 22 | 7-$CF_3$ | H | $CO_2CH_3$ | |
| 23 | 7-$CF_3$ | H | $CO_2Na$ | |
| 24 | 7-OMe | H | $CO_2CH_3$ | |
| 25 | 7-OMe | H | $CO_2Na$ | |
| 26 | 7-$NO_2$ | H | $CO_2CH_3$ | |
| 27 | 7-$NO_2$ | H | $CO_2CH_2CH_3$ | 115–117 |
| 28 | 7-$NO_2$ | H | $CO_2Na$ | |
| 29 | 6-Cl | H | $CON(CH_3)_2$ | 122–125 |
| 30 | 6,7-Cl (mix) | H | $CO_2CH_3$ | 115 |
| 49 | 7-Br | H | $CO_2CH_2CH_3$; $R^7 = CH_2CH_3$ | oil |
| 50 | 6-Br | 7-Br | $CO_2CH_2CH_3$; $R^7 = CH_2CH_3$ | 102–104 |

TABLE 2

Optically Active Compounds of Formula (i)

| Example | $R^1$ | $R^2$ | $R^3$ | Configuration | mp (°C.) |
|---|---|---|---|---|---|
| 31 | 7-Cl | H | $CO_2CH_3$ | (R) | 80 |
| 32 | 7-Cl | H | $CO_2CH_3$ | (S) | 78.6–79.2 |
| 33 | 7-Cl | H | $CO_2Na$ | (R) | 232 |

TABLE 2-continued

Optically Active Compounds of Formula (i)

[Chemical structure: R¹, R² substituted benzene fused to N=C-O-CH₂ linker connected via O to phenyl-O-C*(CH₃)-CO₂CH₃]

| Example | R¹   | R² | R³                 | Configuration | mp (°C.) |
|---------|------|----|--------------------|---------------|----------|
| 34      | 7-Cl | H  | CO$_2$Na           | (S)           | 234–235  |
| 35      | 7-Cl | H  | CO$_2$K            | (R)           |          |
| 36      | 7-Cl | H  | CO$_2$K            | (S)           |          |
| 37      | 7-Br | H  | CO$_2$CH$_3$       | (R)           |          |
| 38      | 7-Br | H  | CO$_2$CH$_3$       | (S)           |          |
| 39      | 7-Br | H  | CO$_2$Na           | (R)           |          |
| 40      | 7-Br | H  | CO$_2$Na           | (S)           |          |
| 41      | 7-Br | H  | CO$_2$K            | (R)           |          |
| 42      | 7-Br | H  | CO$_2$K            | (S)           |          |
| 43      | 7-F  | H  | CO$_2$CH$_3$       | (R)           |          |
| 44      | 7-F  | H  | CO$_2$CH$_3$       | (S)           |          |
| 45      | 7-F  | H  | CO$_2$Na           | (R)           |          |
| 46      | 7-F  | H  | CO$_2$Na           | (S)           |          |
| 47      | 7-F  | H  | CO$_2$K            | (R)           |          |
| 48      | 7-F  | H  | CO$_2$K            | (S)           |          |

UTILITY

Representative compounds of the present invention have been tested in a variety of pre-clinical tests of anti-cancer activity which are indicative of clinical utility. The anti-tumor activity of the compounds of the present invention was evaluated in the animal tumor models described below, including human tumor xenograft models. The anti-tumor activity of the compounds of the present invention is demonstrated in Tables 3 and 4 (below).

The demonstrated effectiveness of the compounds of the present invention in the animal tumor models indicate that the compounds of the present invention may be useful for the treatment of leukemia and solid tumors in man, and, in particular, tumors of the breast and colon. This conclusion is further supported by published analyses correlating pre-clinical test results with clinical efficacy of anti-cancer agents. For example, see: Goldin and Venditti (1980) *Cancer Research* 76: 176–191; Goldin et al. (1981) *Eur. J. Cancer* 17: 129–142; Mattern et al. (1988) *Cancer and Metastasis Review* 7: 263–284; Jackson et al. (1990) *Cancer Investigations* 8: 39–47. Based on these published analyses, the exceptional high level of antitumor activity exhibited by the presently claimed compounds provide strong evidence that the compounds claimed in present invention may have important therapeutic utility in the treatment of cancer in man.

Measurement of Anti-tumor Efficacy

In the murine tumor models described below the anti-tumor activity of the compounds of the present invention was assessed using one or more of the parameters described below.

In the tumor growth inhibition assay the efficacy of test compounds is determined by the extent of tumor growth inhibition in treated versus vehicle-treated control mice. Tumor weights (mg) are estimated from caliper measurements, using the formula for a prolate ellipsoid (mg of tumor weight=(length×width$^2$)/2). Net tumor weights are calculated for each of the treated groups and the vehicle-treated control group by subtracting the initial tumor weight from the final tumor weight when the experiment is terminated. Results are expressed using the formula:

$$\% \text{ Tumor Growth Inhibition} = \left[1 - \frac{\text{mean tumor weight of treated}}{\text{mean tumor weight of control}}\right] \times 100$$

In survival studies the anti-tumor activity is expressed using the formula:

$$\frac{\% \ T/C}{(\text{survival})} = \frac{[\text{MEAN SURVIVAL TIME OF TREATED}]}{[\text{MEAN SURVIVAL TIME OF CONTROLS}]} \times 100$$

In tumor growth delay assays the T/C value was calculated as the median time (days) required for the treated group to reach a predetermined size (750 mg) divided by the median time required for the control group tumors to reach the same predetermined size:

% T/C (tumor growth delay) =

$$\frac{[\text{MEAN TIME FOR TREATED GROUP TO REACH TUMOR SIZE}]}{[\text{MEAN TIME FOR UNTREATED GROUP TO REACH TUMOR SIZE}]} \times 100$$

In some cases tumor growth delay is expressed in "days" calculated by subtracting the median time in days for control group tumors to reach a predetermined weight from the median time for treated group tumors to grow to the same predetermined weight.

In experiments using mouse leukemia models, the activity of test compounds may also be expressed as the percent increase in host life span (%ILS) using the formula:

$$\% \ ILS = \frac{[\text{mean survival time treated group} - \text{mean survival time control group}]}{[\text{mean survival time control group}]} \times 100$$

For subcutaneously growing tumors, the tumor cell kill is calculated as follows:

$$\text{Log}_{10} \text{ kill (total)} = \frac{[T - C \ (\text{days})]}{(3.32)(TD)}$$

where T-C is the tumor growth delay and TD is the tumor doubling time in days.

In the tumor models described below there were 5–10 mice per group of animals.

B16 Melanoma Model: The B16 tumor line arose spontaneously in 1954 on the skin at the base of the ear in a C57BL mouse (NIH Publication No. 84-2635, February, 1984, In Vivo Cancer Models). The tumor line is maintained subcutaneously (s.c.) by serial passage in female C57BL mice. For testing, on day 0, female B6C3F1 mice weighing 18–22 gm. are inoculated intraperitoneally with 0.25 mL of the 1:5 tumor brei. Mice are randomized into groups. A 0.25% Methocel/2% Tween 80 vehicle is used for control and compound formulation. Test compounds and vehicle control are administered intraperitoneally once daily for nine consecutive days beginning on day 1.

Efficacy is expressed as % T/C (survival). Mice that survive 30 days are considered cured and are not included in the calculation of the mean survival time. The NCI criterion for activity is used; for B16 leukemia, a compound having a % T/C (survival) of ≧125 is considered active (Geran et al. *Cancer Chemotherapy Rep.* (1972) 3:1–103).

P388 Leukemia Model: The P388 tumor line originated in 1955 as a lymphocytic leukemia in a female DBA/2 mouse after painting the skin with 3-methylcholanthrene (NIH Publication No. 84-2635, February, 1984, In Vivo Cancer Models). The tumor line is maintained by serial passage in female DBA/2 mice. For testing, on day 0, female CDF1 mice weighing 18-22 gm are inoculated i.p. with $1 \times 10^6$ viable P388 cells harvested from the ascites of passage DBA/2 mice. The mice are randomized into groups. Vehicle control and test compounds are administered i.p. or i.v. once daily for five or nine consecutive days beginning on day 1 (route and days predetermined). A 0.25% Methocel/2% Tween 80 vehicle was used for control and compound formulation.

Efficacy was expressed as a % T/C (survival). Mice that survive 30 days are considered cured and are not included in the calculation of the mean survival time. The NCI criterion for activity are used; a compound providing a T/C (survival) of $\geq 125$ is considered active (Geran et al. *Cancer Chemotherapy Rep.* (1972) 3:1-103).

L 1210 The L1210 tumor line was originally chemically induced in 1948 in the spleen and lymph nodes of a DBA mouse by painting the skin with methylcholanthrene in ethyl ether (NIH Publication No. 84-2635, February 1984: In Vivo Cancer Models). The tumor line is maintained by serial passage in female DBA/2 mice. For testing, on day 0, female CDF1 mice weighing 18-22 gm are inoculated i.p. with $1 \times 10^5$ L1210 cells (0.1 mL/mouse) harvested from the ascites of DBA/2 mice. The mice are randomized into groups. Vehicle control and test compounds are administered i.p. or i.v. once daily for five or nine consecutive days beginning on day 1 (route and days predetermined). A 0.25% Methocel/2% Tween 80 vehicle was used for control and compound formulation.

Efficacy was expressed as a % T/C (survival). Mice that survive 30 days are considered cured and are not included in the calculation of the mean survival time. The NCI criterion for activity are used; a compound providing a T/C (survival) of $\geq 125$ is considered active (Geran et al. *Cancer Chemotherapy Rep.* (1972) 3:1-103).

In Vivo Human Tumor Xenograft Models (MX-1 and DLD-2)

The MX-1 human mammary carcinoma and the DLD-2 human colon carcinoma were originally obtained from a surgically removed primary breast tumor and colon carcinoma, respectively. The human tumor lines were maintained by serial passage in athymic nude mice. The MX-1 human mammary carcinoma is an established tumor used by the NCI. The MX-1 and DLD-2 tumor models have been well characterized.

The mice used in these experiments were outbred Swiss mice or BALB/c mice bearing the nude (nu/nu) gene. On day 0, 30-60 tumor fragments are implanted subcutaneously bilaterally by trocar in female mice (20-25 g). Tumor fragments were prepared from fresh tumors grown subcutaneously in passage mice. Palpable tumors weighing approximately 50 mg appear in the mice within 7-10 days after inoculation. The mice grouped and the test compounds and vehicle control are administered intravenously (iv) once daily on days 3, 5, 7, and 12-16.

Tumor measurements and body weights are recorded once or twice a week. Mice were sacrificed when tumors reached an average weight of 1,500 mg (about day 20).

The efficacy of the test compounds was measured as the % Tumor Growth Inhibition. The criteria of the National Cancer Institute for activity in the in vivo cancer models were used (NIH Publication No. 84-2635, February 1984: In Vivo Cancer Models). Actual tumor regressions (IR= incomplete regression; FR=full regression) indicate excellent to outstanding activity. Tumor growth inhibition of $\geq 90\%$ is considered good to excellent and inhibition of 58-89% is considered moderate to good. Compounds demonstrating <58% growth inhibition are considered inactive.

Pancreatic Ductile Adenocarcinoma (Panc02 and Panc03)

The pancreatic ductal adenocarcinoma tumor line originated from a tumor induced by implant of thread carrying 3-methyl-cholanthrene into the pancreas tissue of a mouse (Corbett et al., *Cancer Research* (1984) 44: 717-726). Tumor fragments were implanted s.c. bilaterally by trocar and the test compounds were administered i.v., p.o., or s.c. beginning 1-3 days after implantation, on a once or twice daily schedule. Drug efficacy was assessed by measuring tumor cell kill, tumor growth delay, and tumor growth inhibition. The mice used were BDF1 females or males of average weight of about 23 g.

Mouse Mammary Adenocarcinoma 16/C (Mam16/C)

The mouse mammary adenocinoma 16/C was originally isolated and maintained in a serial passage by transplantation of metastatic lung foci (Corbett et al., *Cancer Treat. Rep.* (1978) 62: 1471-1488). Tumor fragments were implanted s.c. bilaterally by trocar and 1-3 days later treatment with test compounds was begun. Compounds were administered once or twice daily. Tumors were measured with calipers once or twice weekly. Mice were sacrificed when tumors in the control group exceeded an average weight of 1,500 mg. Anti-tumor activity was assessed by measuring tumor growth delay or % Tumor Growth Inhibition. The mice used were BDF1 or C3H females of average weight of about 23 g.

Mouse Mammary Adenocarcinoma 17 (Mam17)

This tumor line is maintained in the Developmental Therapeutics Program frozen repository, maintained by the Biological Testing Branch, Frederick, Md. (Mucci-LoRosso et al., *Investigational New Drugs* (1990) 8(3): 53-261). Chemotherapy studies in C3H female mice bearing Mam17 tumors were conducted in the same manner as described above for the Mam16/C tumor.

Subcutaneously-implanted Colon 38 Carcinoma (Colon38) and Colon 51 Carcinoma (Colon51)

These tumor lines originated from a tumor chemically induced in the colon of C57BL/6 mouse, induced by repeated s.c. injections of 1,2-dimethylhydrazine (Corbett et al., *Cancer Research* (1975) 35: 2434-2439). Tumor fragments were implanted bilaterally s.c. by trocar and 1-3 days after implantation treatment with test compound was started. Compounds were administered once or twice daily. Tumors were measured with calipers once or twice weekly until tumors in the control group exceeded an average weight of 1,500 mg. Anti-tumor activity was assessed by measuring % Tumor Growth Inhibition. Female CDF1 mice were used for Colon51 studies and BDF1 females for Colon38, with mice generally averaging about 22 g in weight.

TABLE 3

In Vivo Tumor Inhibition Data

| Example | Model | Total Dose (mg/kg) | Route | % Tumor Growth Inhibition | Cures |
|---|---|---|---|---|---|
| 31 | Panc03 | 320 | po | 91 | 2/5 |
| 31 | Mam16c | 400 | po | 100 | — |
| 31 | Mam16c/adr | 480 | po | 91-96 | — |
| 31 | Mam17 | 840 | po | 97 | — |
| 31 | Colon38 | 495 | po | 100 | 3/5 |
| 31 | Colon51 | 480 | po | 80 | — |

TABLE 3-continued

In Vivo Tumor Inhibition Data

| Example | Model | Total Dose (mg/kg) | Route | % Tumor Growth Inhibition | Cures |
|---|---|---|---|---|---|
| 8 | Panc02 | 600 | iv | 91 | — |
| 8 | Panc03 | 210 | iv | 100 | — |
| 8 | Panc03 | 490 | po | 100 | 1/5 |
| 8 | Panc03 | 329 | po | 100 | 4/6 |
| 8 | Colon38 | 546 | iv | 100 | 3/5 |
| 8 | Colon38 | 273 | iv | 100 | 2/5 |
| 8 | Colon51 | 980 | po | 100 | 1/5 |
| 8 | Colon51 | 600 | ip | 94 | — |
| 8 | Mam16c | 525 | iv | 97 | — |
| 8 | Mam17 | 620 | iv | 98 | — |
| 8 | Mam17 | 710 | po | 98 | — |
| 8 | MX1 | 332 | iv | 70 | — |
| 18 | Panc03 | 600 | po | 98 | — |
| 21 | Panc03 | 287 | po | 69 | — |
| 20 | Panc03 | 1590 | po | 83 | — |
| 29 | Mam17 | 1525 | po | 83 | — |
| 29 | Colon38 | 1795 | po | 100 | 3/5 |
| 33 | Colon38 | 260 | po | 91 | — |

TABLE 4

In Vivo Data Tumor Inhibition Data

| Example | Model | Dose (mg/kg /day) | Route | % T/C | Cures |
|---|---|---|---|---|---|
| 31 | L1210 | 500 | ip | 147 | 1/6 |
| 31 | B16 | 500 | ip | 138 | — |
| 31 | P388 | 500 | ip | 187 | 1/6 |
| 32 | L1210 | 50 | ip | 262 | 1/6 |
| 30 | L1210 | 200 | ip | 281 | 2/6 |
| 30 | B16 | 200 | ip | 151 | — |
| 5 | L1210 | 200 | ip | 154 | 2/6 |
| 5 | B16 | 100 | ip | 142 | — |
| 27 | L1210 | 100 | ip | 138 | — |
| 3 | L1210 | 200 | ip | 239 | 2/6 |
| 3 | B16 | 50 | ip | 148 | — |
| 13 | L1210 | 50 | ip | 232 | — |
| 13 | B16 | 50 | ip | 146 | — |
| 49 | L1210 | 200 | ip | 256 | — |
| 50 | L1210 | 100 | ip | 153 | — |

Dosage and Formulation

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 1 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in *Remington's Pharmaceutical Sciences*, Mack Publishing Company, a standard reference text in this field.

Useful pharmaceutical dosage forms for administration of the compounds of this invention can be illustrated as follows:

Capsules: Capsules are prepared by filling standard two-piece hard gelatin capsules each with 100 milligrams of powdered active ingredient, 175 milligrams of lactose, 24 milligrams of talc, and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are washed and dried.

Tablets: Tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstrach and 98 milligrams of lactose. Appropriate coatings may be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

In the present disclosure it should be understood that the specified materials and conditions are important in practicing the invention but that unspecified materials and conditions are not excluded so long as they do not prevent the benefits of the invention from being realized.

What is claimed is:

1. A pharmaceutical composition, comprising: a pharmaceutically acceptable carrier and a therapeutically effective amount of a compound of formula (ii):

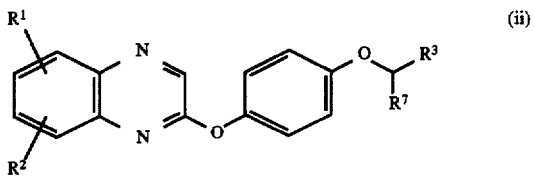

or enantiomeric or diastereomeric forms thereof, or mixtures of enantiomeric or diastereomeric forms thereof, and pharmaceutically acceptable salts thereof, wherein:

$R^1$ and $R^2$ independently are H, F, Cl, Br, $CF_3$, $OCH_3$, or $NO_2$;

$R^3$ is $CO_2H$, $CO_2M$, $CONHCH_2CH_2OH$, $CONHCH_2CH_2CH_2N(CH_3)_2$, $CONHC(CH_2OH)_2CH_3$, $CONR^4R^5$, or $CO_2R^6$;

M is a pharmaceutically acceptable counterion;

$R^4$ and $R^5$ independently are alkyl of 1–4 carbon atoms, cycloalkyl of 5–8 carbon atoms, phenyl, or benzyl;

$R^6$ is alkyl of 1–4 carbon atoms, cycloalkyl of 5–8 carbon atoms, alkenyl or alkynyl of 3–4 carbon atoms, phenyl or benzyl;

$R^7$ is alkyl of 1–4 carbon atoms; and, the composition is suitable for internal administration and is in the form of a capsule, tablet, or liquid dosage.

2. A pharmaceutical composition of claim 1, wherein:

$R^1$ and $R^2$ independently are H, F, Cl, Br, $CF_3$, $OCH_3$, or $NO_2$;

$R^3$ is $CO_2H$, $CO_2M$, $CONHCH_2CH_2OH$, $CONHCH_2CH_2CH_2N(CH_3)_2$, $CONHC(CH_2OH)_2CH_3$, $CONR^4R^5$, or $CO_2R^6$;

M is a pharmaceutically acceptable counterion;

$R^4$ and $R^5$ independently are alkyl of 1–4 carbon atoms, cycloalkyl of 5–8 carbon atoms, phenyl, or benzyl;

$R^6$ is alkyl of 1–4 carbon atoms, cycloalkyl of 5–8 carbon atoms, alkenyl or alkynyl of 3–4 carbon atoms, phenyl or benzyl; and, $R^7$ is $CH_3$.

3. A pharmaceutical composition of claim 2, wherein:

$R^1$ is 7-Cl, 7-Br, or 6-Cl;

$R^2$ is H;

$R^3$ is $CO_2CH_3$, $CO_2M$, $CONHCH_2CH_2OH$, $CONHCH_2CH_2CH_2N(CH_3)_2$, or $CONHC(CH_2OH)_2CH_3$;

M is Na, K, Li, $NH_4$, $MeNH_3$, or $Me_2NH_2$; and, $R^7$ is $CH_3$.

4. A pharmaceutical composition of claim 3 wherein the compound is selected from the group consisting of:

a compound of formula (ii) wherein $R^1$ is 7-Cl, $R^2$ is H, $R^3$ is $CO_2CH_3$, $R^7$ is $CH_3$, (racemic);

a compound of formula (ii) wherein $R^1$ is 7-Cl, $R^2$ is H, $R^3$ is $CO_2CH_3$, $R^7$ is $CH_3$, (R);

a compound of formula (ii) wherein $R^1$ is 7-Cl, $R^2$ is H, $R^3$ is $CO_2CH_3$, $R^7$ is $CH_3$, (S);

a compound of formula (ii) wherein $R^1$ is 7-Br, $R^2$ is H, $R^3$ is $CONHCH_2CH_2OH$, $R^7$ is $CH_3$, (R);

a compound of formula (ii) wherein $R^1$ is 7-Br, $R^2$ is H, $R^3$ is $CONHCH_2CH_2OH$, $R^7$ is $CH_3$, (S);

a compound of formula (ii) wherein $R^1$ is 7-Br, $R^2$ is H, $R^3$ is $CONHCH_2CH_2OH$, $R^7$ is $CH_3$, (racemic);

a compound of formula (ii) wherein $R^1$ is 7-Br, $R^2$ is H, $R^3$ is $CONHCH_2CH_2CH_2N(CH_3)_2$, $R^7$ is $CH_3$; and, a compound of formula (ii) wherein $R^1$ is 7-Br, $R^2$ is H, $R^3$ is $CONHC(CH_2OH)_2CH_3$, $R^7$ is $CH_3$.

5. A pharmaceutical composition according to claim 4, wherein the composition is in the form of a capsule.

6. A pharmaceutical composition according to claim 5, wherein the capsule is a hard gelatin capsule or a soft gelatin capsule.

7. A pharmaceutical composition according to claim 4, wherein the composition is in the form of a liquid dosage.

8. A pharmaceutical composition according to claim 7, wherein the liquid dosage is sterile.

9. A pharmaceutical composition according to claim 4, wherein the composition is in the form of a tablet.

10. A pharmaceutical composition according to claim 9, wherein the tablet is coated, whereby said coating increases palatability or delays absorption.

11. A method of treating a solid tumor or lymphoid leukemia in a mammal comprising administering to a mammal bearing such a tumor or leukemia, a therapeutically effective amount of a pharmaceutical composition of claim 1, wherein the solid tumor is selected from solid tumors of the breast, colon, pancreas, or melanoma.

12. A method of treating a solid tumor or lymphoid leukemia in a mammal comprising administering to a mammal bearing such a tumor or leukemia, a therapeutically effective amount of a pharmaceutical composition of claim 2, wherein the solid tumor is selected from solid tumors of the breast, colon, pancreas, or melanoma.

13. A method of treating a solid tumor or lymphoid leukemia in a mammal comprising administering to a mammal bearing such a tumor or leukemia, a therapeutically effective amount of a pharmaceutical composition of claim 3, wherein the solid tumor is selected from solid tumors of the breast, colon, pancreas, or melanoma.

14. A method of treating a solid tumor or lymphoid leukemia in a mammal comprising administering to a mammal bearing such a tumor or leukemia, a therapeutically effective amount of a pharmaceutical composition of claim 4, wherein the solid tumor is selected from solid tumors of the breast, colon, pancreas, or melanoma.

15. A method of treating a solid tumor or lymphoid leukemia in a mammal comprising administering to a mammal bearing such a tumor or leukemia, a therapeutically effective amount of a pharmaceutical composition of claim 5, wherein the solid tumor is selected from solid tumors of the breast, colon, pancreas, or melanoma.

16. A method of treating a solid tumor or lymphoid leukemia in a mammal comprising administering to a mammal bearing such a tumor or leukemia, a therapeutically effective amount of a pharmaceutical composition of claim 7, wherein the solid tumor is selected from solid tumors of the breast, colon, pancreas, or melanoma.

17. A method of treating a solid tumor or lymphoid leukemia in a mammal comprising administering to a mammal bearing such a tumor or leukemia, a therapeutically effective amount of a compound of formula (ii):

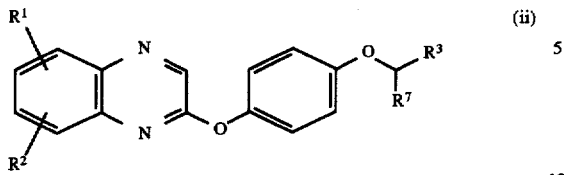

or enantiomeric or distereomeric forms thereof, or mixtures of enantiomeric or diastereomeric forms thereof, and pharmaceutically acceptable salts thereof, wherein:

$R^1$ and $R^2$ independently are H, F, Cl, Br, $CF_3$, $OCH_3$, or $NO_2$;

$R^3$ is $CO_2H$, $CO_2M$, $CONHCH_2CH_2OH$, $CONHCH_2CH_2CH_2N(CH_3)_2$, $CONHC(CH_2OH)_2CH_3$, $CONR^4R^5$, or $CO_2R^6$;

M is a pharmaceutically acceptable counterion;

$R^4$ and $R^5$ independently are alkyl of 1–4 carbon atoms, cycloalkyl of 5–8 carbon atoms, phenyl, or benzyl;

$R^6$ is alkyl of 1–4 carbon atoms, cycloalkyl of 5–8 carbon atoms, alkenyl or alkynyl of 3–4 carbon atoms, phenyl or benzyl;

$R^7$ is alkyl of 1–4 carbon atoms; and, the solid tumor is selected from solid tumors of the breast, colon, pancreas, or melanoma.

18. A method according to claim 17, wherein:

$R^1$ and $R^2$ independently are H, F, Cl, Br, $CF_3$, $OCH_3$, or $NO_2$;

$R^3$ is $CO_2H$, $CO_2M$, $CONHCH_2CH_2OH$, $CONHCH_2CH_2CH_2N(CH_3)_2$, $CONHC(CH_2OH)_2CH_3$, $CONR^4R^5$, or $CO_2R^6$;

M is a pharmaceutically acceptable counterion;

$R^4$ and $R^5$ independently are alkyl of 1–4 carbon atoms, cycloalkyl of 5–8 carbon atoms, phenyl, or benzyl;

$R^6$ is alkyl of 1–4 carbon atoms, cycloalkyl of 5–8 carbon atoms, alkenyl or alkynyl of 3–4 carbon atoms, phenyl or benzyl;

$R^7$ is $CH_3$.

19. A method according to claim 18, wherein:

$R^1$ is 7-Cl, 7-Br, or 6-Cl;

$R^2$ is H;

$R^3$ is $CO_2CH_3$, $CO_2M$, $CONHCH_2CH_2OH$, $CONHCH_2CH_2CH_2N(CH_3)_2$, or $CONHC(CH_2OH)_2CH_3$;

M is Na, K, Li, $NH_4$, $MeNH_3$, or $Me_2NH_2$;

$R^7$ is $CH_3$.

20. A method according to claim 19 wherein the compound is selected from the group consisting of:

a compound of formula (ii) wherein $R^1$ is 7-Cl, $R^2$ is H, $R^3$ is $CO_2CH_3$, $R^7$ is $CH_3$, (racemic);

a compound of formula (ii) wherein $R^1$ is 7-Cl, $R^2$ is H, $R^3$ is $CO_2CH_3$, $R^7$ is $CH_3$, (R);

a compound of formula (ii) wherein $R^1$ is 7-Cl, $R^2$ is H, $R^3$ is $CO_2CH_3$, $R^7$ is $CH_3$, (S);

a compound of formula (ii) wherein $R^1$ is 7-Br, $R^2$ is H, $R^3$ is $CONHCH_2CH_2OH$, $R^7$ is $CH_3$, (R);

a compound of formula (ii) wherein $R^1$ is 7-Br, $R^2$ is H, $R^3$ is $CONHCH_2CH_2OH$, $R^7$ is $CH_3$, (S);

a compound of formula (ii) wherein $R^1$ is 7-Br, $R^2$ is H, $R^3$ is $CONHCH_2CH_2OH$, $R^7$ is $CH_3$, (racemic);

a compound of formula (ii) wherein $R^1$ is 7-Br, $R^2$ is H, $R^3$ is $CONHCH_2CH_2CH_2N(CH_3)_2$, $R^7$ is $CH_3$;

a compound of formula (ii) wherein $R^1$ is 7-Br, $R^2$ is H, $R^3$ is $CONHC(CH_2OH)_2CH_3$, $R^7$ is $CH_3$.

* * * * *